United States Patent
Oakes et al.

(10) Patent No.: US 7,091,172 B2
(45) Date of Patent: Aug. 15, 2006

(54) TEXTILE LAUNDERING COMPOSITION COMPRISING A SELF-CROSSLINKING CATIONIC POLYMER

(75) Inventors: John Oakes, Winsford (GB); Matthew Sugdon, Basingstoke (GB)

(73) Assignee: Unilever Home & Personal Care USA Division of Conopco, Inc., Greenwich, CT (US)

( * ) Notice: Subject to any disclaimer, the term of this patent is extended or adjusted under 35 U.S.C. 154(b) by 198 days.

(21) Appl. No.: 10/450,076

(22) PCT Filed: Dec. 3, 2001

(86) PCT No.: PCT/EP01/14378

§ 371 (c)(1),
(2), (4) Date: Jun. 9, 2003

(87) PCT Pub. No.: WO02/48303

PCT Pub. Date: Jun. 20, 2002

(65) Prior Publication Data

US 2004/0045093 A1    Mar. 11, 2004

(30) Foreign Application Priority Data

Dec. 11, 2000 (GB) .................................. 0030177.0
Apr. 11, 2001 (GB) .................................. 0109142.0

(51) Int. Cl.
*C11D 3/37* (2006.01)

(52) U.S. Cl. ..................... 510/521; 510/276; 510/515; 510/504

(58) Field of Classification Search ................ 510/276, 510/521, 515, 504
See application file for complete search history.

(56) References Cited

U.S. PATENT DOCUMENTS

| 3,594,355 | A | * | 7/1971 | Vandenberg et al. ........ 528/109 |
| 3,694,258 | A | * | 9/1972 | Vandenberg et al. ........ 442/104 |
| 5,160,733 | A | | 11/1992 | Berthiaume et al. |
| 5,354,335 | A | | 10/1994 | Lipshitz et al. |

FOREIGN PATENT DOCUMENTS

| EP | 0 978 556 | 2/2000 |
| GB | 2 039 938 | 8/1980 |
| WO | 98/12295 | 3/1998 |
| WO | 99/06519 | 2/1999 |
| WO | 00/15746 | 3/2000 |
| WO | 00/49122 | 8/2000 |
| WO | 01/25386 | 4/2001 |

OTHER PUBLICATIONS

UK Search Report No. GB 0109142.0 dated Sep. 17, 2001 —1 p.
International Search Report No. PCT/EP 01/14378 dated May 28, 2002 —3 pp.
Co-pending U.S. Appl. No. 10/450,075, filed Jun. 9, 2003, Oakes, et al., Textile Care Composition.

* cited by examiner

*Primary Examiner*—Charles Boyer
(74) *Attorney, Agent, or Firm*—Alan A. Bornstein

(57) ABSTRACT

A process for the treatment of non-keratinaceous textiles, preferably cellulosic fibers, which comprises the step of treating the textiles with a composition which comprises: a self-crosslinking polymer and a nucleophilic species (preferably a polymer comprising at least one protected thiol group), and a textile compatible carrier. Under domestic washing conditions the polymer forms reactive thiol groups which are capable of causing covalent cross-linking with the polymer. Preferably, the thiol group is protected as an isothiouronium group.

10 Claims, No Drawings

TEXTILE LAUNDERING COMPOSITION COMPRISING A SELF-CROSSLINKING CATIONIC POLYMER

FIELD OF THE INVENTION

This invention relates to fabric care compositions, including detergent compositions and laundry rinse compositions. The invention also relates to methods of treating fabric using the compositions of the invention.

BACKGROUND AND PRIOR ART

The appearance of coloured fabrics, e.g., clothing, bedding, household fabrics like table linens is one of the areas of concern to consumers. Indeed, upon typical consumer's uses of the fabrics such as wearing, washing, rinsing and/or tumble-drying of fabrics, lead to changes in fabric appearance, which is at least partly due to loss of colour shade intensity, fidelity and color definition.

Such a problem of colour loss is even more acute in laundry treatment after multiwash cycles, especially for dark colours, such as blacks, reds, blues, and greens.

Several mechanisms have been speculated upon for colour loss and various means have been proposed to prevent or reduce the extent of the loss or transfer of colour. For example, colour fixatives, known in the dyeing industry have been proposed, as have agents (such as PVP) to hold colour materials in solution to prevent re-deposition or to prevent abrasion between fibers. It has also been suggested to add bleaching agents to wash liquor to bleach any dye that enters solution.

One cause of colour loss is the use of an inappropriate detergent composition. Thus, many manufacturers produce 'colour care' formulations that do not contain bleaches. Despite this, colour damage remains a significant problem in the eyes of consumers.

WO 00/15746 (P&G), filed 15$^{th}$, September 1998, published 23$^{rd}$ March 2000, discloses fabric care compositions, which comprise low molecular weight polyamines for colour care. It is believed that the polyamines intercept peroxygen bleaching. A dye fixative may also be present in the compositions disclosed, as may an 'abrasion reducing polymer' such as the N-heterocyclic polymer PVP (see examples 50–53 in table XII).

In order to overcome these problems it has also been proposed to use self cross-linking agents, to treat the fabric. These are believed to form a protective matrix around the fibers of the fabric, which reduces fiber damage. It is believed that this structure restricts relative movement of the textile fibers and consequently reduces damage to the textile fibers during the laundering process. It is also believed that this reduces pilling and provides shrink resistance.

It is further believed that the structure prevents apparent colour loss by retarding damage to the fibers leading to a rough fiber surface which would give the appearance of colour lose due to a modification of the manner in which light is scattered from the fiber surface.

Laundry detergent compositions containing reactive polyamide-polyamine fabric treatment agents are known. The compositions are claimed to impart improved overall appearance to fabrics laundered using the detergent compositions, in terms of surface appearance properties such as pill/fuzz reduction and anti-fading. Other cationic self cross-linking agents are known.

Polyamine epichlorohydrin resins (PAE) are effective self cross-linking agents, which is known to reduce fiber damage. However under certain circumstances use of PAE can lead to changes in the appearance of dyed fabrics as regards their colour. There is a need to overcome this problem.

WO 98/12295 (P&G: published 1988) discloses the combination of dye fixing agents and amino-functional polymers to improve the colour appearance of laundered fabrics especially after multi-wash cycles. One possible mechanism of action is that the dye fixative locks the dyestuff to the surface preventing colour loss, while the amino functional polymer prevents bleaches having a detrimental effect on dyes. There is no suggestion in this document that there is any reaction between the amini-functional material and the dye fixative.

BRIEF DESCRIPTION OF THE INVENTION

The present invention is based on the finding that reaction of a cationic self-crosslinking agent with a nucleophile significantly reduces the tendency of the self-crosslinking agent to cause colour damage. Surprisingly, this also improves the efficiency of the self-crosslinking reaction enabling it to be performed at lower temperatures. These lower temperatures further reduce the extent of fabric damage.

It is believed that the propensity of the cationic self-crosslinking agents (such as PAE) to change the colour of dyes is in part due to presence of a cationic charge on the molecule. It is believed that the self-crosslinking agents are both attracted to anionic charges present on many dyestuffs, leading to a hue change, and that these materials can also bind dyes and soil from solution leading to a loss of colour definition.

According to the present invention, there is provided a laundering process for the treatment of non-keratinaceous textiles, which comprises the step of treating the textiles with a composition comprising:
a) a self-crosslinking cationic polymer,
b) a nucleophilic species capable of reacting with the polymer (a), said nucleophilic species being protected by a group which is labile under the conditions of pH and temperature in the laundering process, and,
c) a textile compatible carrier.

The present invention further provides a composition for this treatment which comprises:
a) a self-crosslinking cationic polymer
b) a nucleophilic species capable of reacting with polymer (a), said nucleophilic species being protected by a group which is labile under the conditions of pH and temperature in the laundering process, and,
c) a textile compatible carrier.

We believe that reaction with a nucleophile reduces the cationic charge on the self-crosslinking agent and this both reduced the tendency to cause colour damage and other negatives caused by soil and dye binding, and, improves the reaction rate by forming a more reactive species.

DETAILED DESCRIPTION OF THE INVENTION

The textiles, which are intended to be treated in the present invention, preferably comprise cellulosic fibres, preferably from 1% to 100% cellulosic fibres (more preferably 5% to 100% cellulosic fibres, most preferably 40% to 100%). When the textile contains less than 100% cellulosic fibres, the balance comprises other fibres or blends of fibres suitable for use in garments such as polyester, for example. Preferably, the cellulosic fibres are of cotton or regenerated cellulose such as viscose.

The laundering processes of the present invention include the large scale and small scale (e.g. domestic) cleaning of textiles. Preferably, the processes are domestic.

Self-crosslinking Cationic Polymers

Preferably, the reactive cationic polymer is an amine- or amide-epichlorohydrin resin or derivative thereof. Preferably these cationic polymers have a weight average mean molecular weight of from 300 to 1,000,000 Dalton.

The preferred epichlorohydrin resins of the invention are sometimes referred to as amine-epichlorohydrin resins and polyamine-epichlorohydrin (PAE) resins (the two terms being used synonymously) although these terms encompass both the amine and amide resins of the invention and their derivatives. The resins may also have a mixture of amine and amide groups.

The amine- or amide-epichlorohydrin resins preferably have one or more functional groups capable of forming azetidinium groups and/or one or more azetidinium functional groups. These have the structure given below:

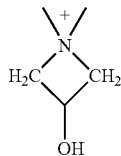

Alternatively, or additionally, the resins may have one or more functional groups that contain epoxide groups or derivatives thereof e.g. Kymene™ 450 (ex Hercules)

Suitable polyamine-epichlorohydrin (PAE) resins include those described in "Wet Strength Resins and Their Application", pp 16–36, ed. LL Chan, Tappi Press, Atlanta, 1994. Suitable resins can be identified by selecting those resins, which impart increased wet strength to paper, after treatment, in a relatively simple test.

Amine- or amide-epichlorohydrin resins having an epoxide functional group or derivative thereof are suitable for use according to the invention.

A particularly preferred class of amine- or amide-epichlorohydrin resins for use in the invention are secondary amine- or amide-based azetidinium resins, for example those resins derived from a polyalkylene polyamine e.g. diethylenetriamine (DETA), a polycarboxylic acid e.g. adipic acid or other dicarboxylic acids, and epichlorohydrin.

Other polyamines or polyamides can also be advantageously used in the preparation of suitable PAE resins.

Another preferred class of amine-epichlorohydrin resins suitable for use in the invention is that having an epoxide functional group or derivative thereof e.g. a chlorohydrin group.

The resin may be a PDAA-epichlorohydrin resin or a PMDAA-epichlorohydrin resin. PDAA is poly(diallylamine) and PMDAA is poly(methyldiallyl (amine)).

The resin is preferably present in the product in a sufficient quantity to give an amount of 0.0005–5% by weight on the fabric based on the weight of fabric (owf), more preferably 0.001–2% owf. The amount of the resin in the composition required to achieve the above % by weight on fabric will typically be in the range 0.01% to 35% by weight, preferably 0.1% to 13.5% by weight.

Examples of suitable azetidinium containing materials are those available as the 'Hercosett'™ and 'Listrilan'™ polymers. These are believed to be amine or amide-epichlorohydrin resin having one or more azetidinium functional groups.

Nucleophile Species Capable of Reacting with the Polymer

Preferred nucleophilic species are those containing reactive thiol, amino (both primary and secondary), thiosulphate, phosphonate, or some carboxylates. These species can be polymers or can be of relatively low molecular weight.

Those having thiol, amino or thiosulphate reactive species are preferred due to their ease of reaction. Those having phosphonate or carboxylate reactive species are less preferred as at lower temperatures they have a tendency merely to complex through ionic interactions rather than cross-link through the formation of a covalent bond.

The nucleophile is protected as self-crosslinking reactions would otherwise occur between the nucleophilic species.

Particularly preferred nucleophile species are those having a protected thiol group with a suitably labile leaving group. It is most preferable that the protected thiol group comprises an isothiouronium group.

Use of an isothiouronium containing polymer, or other thiol group protected by another suitably labile leaving group, in a composition which further comprises a textile compatible carrier is believed to reduce fiber damage and/or improve the dimensional stability of cellulosic textiles following domestic laundry. For illustrative purposes, the compositions of the present invention will be further described below with reference to those comprising at least one polymer comprising at least one isothiouronium group.

The isothiouronium group fulfils the requirements of a suitable protecting group as it is labile under conditions of pH and temperature found in domestic laundry. Typical conditions encountered are a pH from 8 to 11 and a temperature of 10 to 80 Celsius. Slightly higher temperatures are encountered under some ironing and domestic drying conditions. It is preferable that the protecting group is sufficiently labile that it leaves when the polymer is exposed to a pH of above 8 at a temperature of below 50 Celsius.

Isothiouronium salts are advantageous in that they are can heat cured, for example by a domestic ironing or tumble drying procedure. If used, heat curing is preferably carried out at a temperature in the range of from 50 to 100° C., more preferably from 80 to 100° C.

The polymer is preferably present in the textile care composition in a sufficient quantity to give an amount of 0.0005% to 5% by weight on the textile based on the weight of the textile, more preferably 0.001% to 2% by weight on textile.

Preferably, the polymers have a weight average mean molecular weight of from 300 to 1,000,000 Dalton.

As explained above, the polymers of the invention undergo elimination under mildly alkaline conditions, such as those encountered during a domestic laundering process, to produce thiol intermediates. These can then react as nucleophiles with the self cross-linking polymer (for example PAE). This two-component reaction has two advantages. Firstly, the reaction proceeds quickly and at lower temperatures due to the ease of reactivity between the components (for example between PAE and a thiol). Secondly, the product obtained does not suffer the disadvantage of a residual positive charge which can cause dye damage and assist in the adherence of soils and dyestuffs from solution.

Preferably, the molecular weight of the thiol-containing polymers used is such that any unpleasant odor component associated with the thiol intermediate is not sufficiently volatile to affect the efficacy of the textile care composition.

As will be illustrated hereafter the backbone of the polymer can take several forms. Preferred polymers according to the invention are based on either polypropylene oxide or polyethyleneimine. Polypropylene polymers are preferred as they give a softer feel to treated fabrics.

Preferably, the protected thiol polymers used in the compositions of the invention have two or more reactive end groups. It had been found preferable to employ polymers with three or more reactive end groups.

Formula (I) below shows an illustrative protected-thiol polymer based on polypropylene oxide.

As can be seen from the illustrative Formula (I) the molecules of that series of embodiments contain a number of linked backbones (in this case three), a linker group towards the free end of the backbone and the protected thiol group at the terminal. As will be understood from the forgoing, at high pH the urea leaves the protected thiol group.

Formula (I):

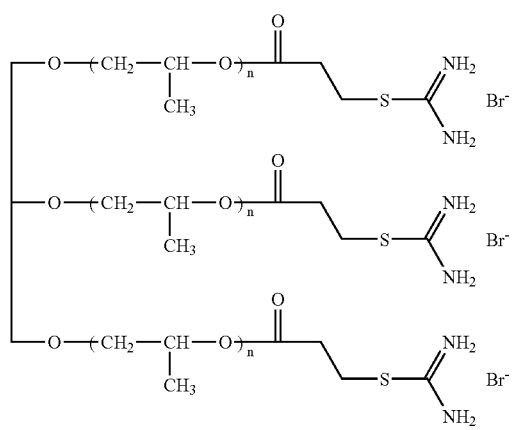

While it is preferred that the protected thiol is in a terminal position (as in Formula I above) it is possible to produce polymers in which the protected thiol is non-terminal (as in Formula II, below).

By way of example, Formula II shows how a protected thiol group may be introduced into a polyethyleneimine by reaction with chloropropionyl chloride followed by reaction of the product with thiourea.

Formula (II):

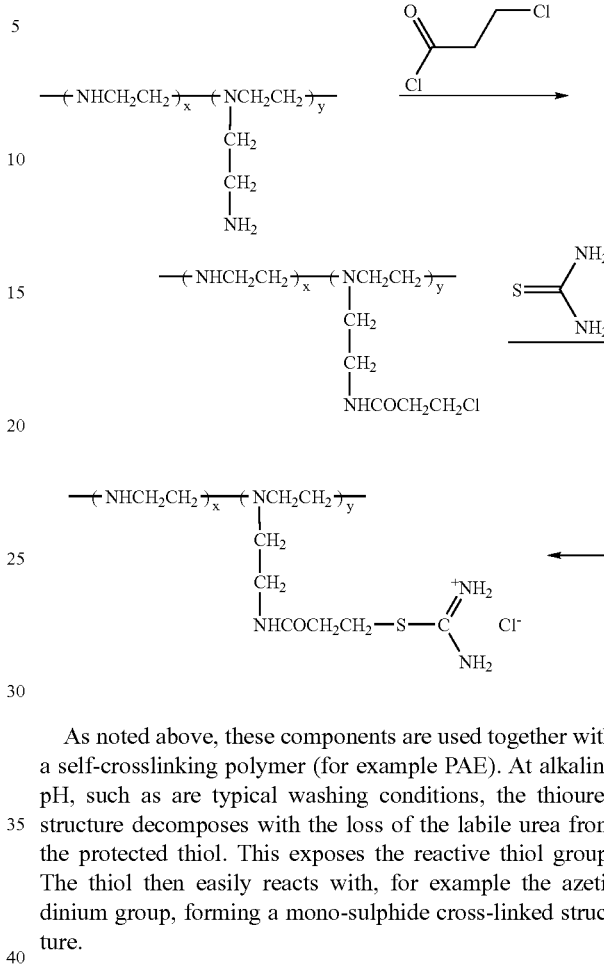

As noted above, these components are used together with a self-crosslinking polymer (for example PAE). At alkaline pH, such as are typical washing conditions, the thiourea structure decomposes with the loss of the labile urea from the protected thiol. This exposes the reactive thiol group. The thiol then easily reacts with, for example the azetidinium group, forming a mono-sulphide cross-linked structure.

Details of other commercially available polymers which can act as backbones for the isothiouronium containing polymers are as follows:

Dethylenetriamine/adipic Acid Polymer Derived Nucleophiles:

Polymers based on diethylenetriamine/adipic acid are reacted with chloropropionyl chloride and thiourea to give isothiouronium-containing polymers, as shown in the figure below.

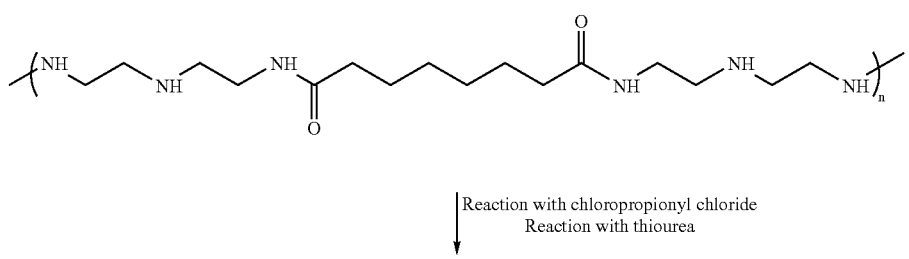

Reaction with chloropropionyl chloride
Reaction with thiourea

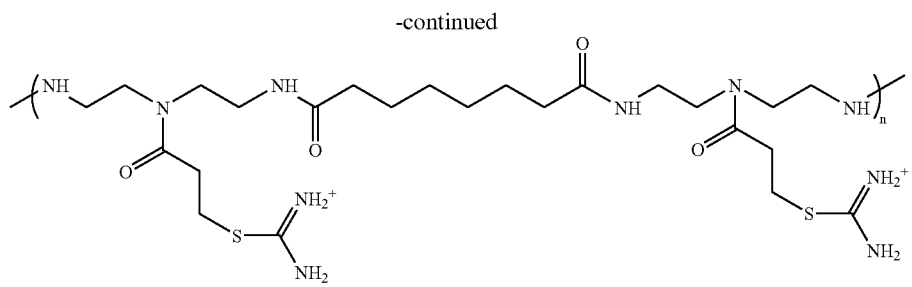

As with the illustrative embodiments discussed above, these polymers lose the protective group under the conditions of the wash and the exposed thiol group can react with the self-crosslinking polymer.

Nucleophiles Derived from Amino Functional Dendrimers:

Embodiments of the invention are not limited to polymers having a relatively small number of terminal or mid chain protected groups. Dendrimers containing a multiplicity of amino groups can be reacted with chloro-acetyl chloride and thiourea to give suitable isothiouronium polymers. Suitable starting molecules include Lupasols,™ (ex-BASF) Star-Burst™ (ex-Dow) or DAB-Am™ (ex-DSM) molecules.

The backbone of the nucleophile-bearing polymer can be a carbohydrate or carbohydrate derivative as shown below.

Nucleophiles Derived from Chitosan:

Chitosan can be reacted with chloropropionyl chloride and then with thiourea to give a water soluble cationic product having pendant isothiouronium groups.

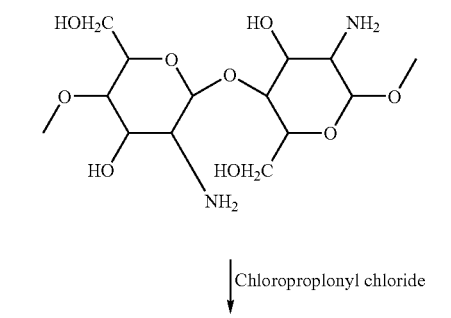

Chloroproplonyl chloride

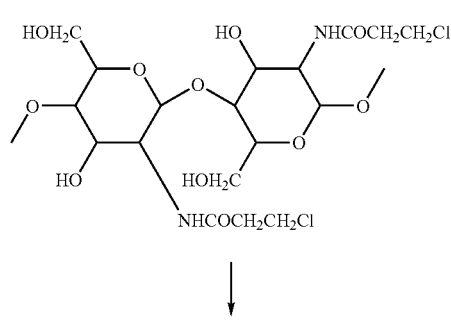

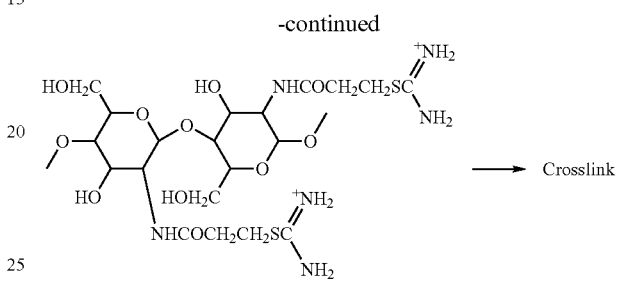

→ Crosslink

It is not necessary to synthesize the polymers from amines as described above.

Nucleophiles Derived from Poly(Vinyl Alcohol):

PVA can be reacted with chloropropionyl chloride and then reacted with thiourea to give a cationic water-soluble polymer with a labile urea residue. As in the previous descriptions the labile urea may be mid-chain or terminal.

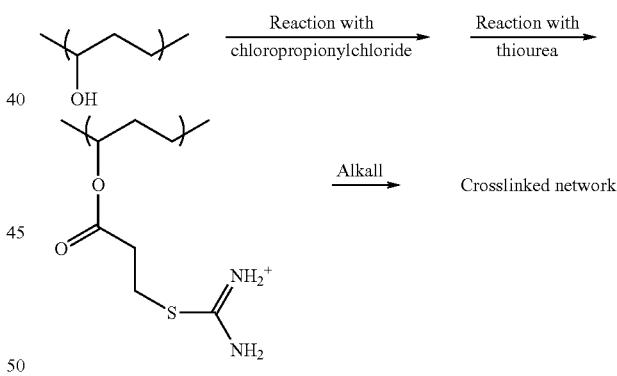

Non-polymeric Nucleophile Species:

It is known to add chelating agents to laundry compositions to reduce color shifting, especially for the reduction of bluing of direct red dyes when tap water containing dissolved metals such as iron, copper, and the like is used.

Chelating agents suitable for use herein can be selected from the group consisting of amino-carboxylates, imino-disuccinates, hydroxy-carboxylates (especially citrates), phosphonates (especially the amino-phosphonates), poly-functionally-substituted aromatic chelating agents, phosphates, and mixtures thereof.

Without intending to be bound by theory, it is believed that a part of the benefit of these materials is due in part to their exceptional ability to remove iron, copper and manganese ions from washing solutions by formation of soluble chelates. Commercial chelating agents for use herein include imino-disuccinate TP© from Bayer; DEQUEST™ series, and chelants from Monsanto, DuPont, and Nalco, Inc.

Amino-carboxylates useful as optional chelating agents are further illustrated by ethylene-diaminetetracetates, N-hydroxyethyl-ethylene-diaminetriacetates, nitrilotriacetates, ethylene-diamine tetraproprionates, triethylene-tetraamine-hexacetates, diethylene-triamine-pentaacetates, and ethanol-diglycines, alkali metal, ammonium, and substituted ammonium salts thereof. Polyfunctionally-substituted aromatic chelating agents are also useful in the compositions herein. See U.S. Pat. No. 3,812,044 issued May 21, 1974, to Connor et al. and U.S. Pat. No. 6,099,587 issued Aug. 8, 2000 to Scialla et al.; both of which are here incorporated by references for further useful examples.

Amino-phosphonates are also suitable for use as chelating agents in the compositions of the invention when at least low levels of total phosphorus are permitted in detergent compositions, and include the ethylene-diaminetetrakis (methylene-phosphonates) and the diethylene-triaminepentakis (methylene-phosphonates). If utilized, chelating agents or transition-metal-selective sequestrants will preferably comprise from about 0.001% to about 10%, more preferably from about 0.05% to about 1% by weight of the compositions herein.

Carboxymethyloxy succinates, and alkali metal, ammonium, substituted ammonium and alkanolamine Salts thereof are also suitable for use as chelating agents in the composition of the invention. See U.S. Pat. No. 3,692,685, issued Sep. 19, 1972 to Lamberti et al., which is here incorporated by reference.

Textile Compatible Carriers

In the context of the present invention the term "textile compatible carrier" is a component which can assist in the interaction of the first component with the textile. The carrier can also provide benefits in addition to those provided by the first component e.g. softening, cleaning etc. The carrier may be a water or a detergent-active compound or a textile softener or conditioning compound or other suitable detergent or textile treatment agent.

If the composition of the invention is to be used in a laundry process as part of a conventional textile treatment product, such as a detergent composition, the textile-compatible carrier will typically be a detergent-active compound. Whereas, if the textile treatment product is a rinse conditioner, the textile-compatible carrier will be a textile softening and/or conditioning compound.

If the composition of the invention is to be used before, or after, the laundry process it may be in the form of a spray or foaming product.

The polymer is preferably used to treat the textile in the rinse cycle of a laundering process. The rinse cycle preferably follows the treatment of the textile with a detergent composition.

Detergent Active Compounds As Carriers:

If the composition of the present invention is in the form of a detergent composition, the textile-compatible carrier may be chosen from soap and non-soap anionic, cationic, nonionic, amphoteric and zwitterionic detergent active compounds, and mixtures thereof.

Many suitable detergent active compounds are available and are fully described in the literature, for example, in "Surface-Active Agents and Detergents", Volumes I and II, by Schwartz, Perry and Berch.

The preferred textile-compatible carriers that can be used are soaps and synthetic non-soap anionic and nonionic compounds.

Anionic surfactants are well-known to those skilled in the art. Examples include alkylbenzene sulphonates, particularly linear alkylbenzene sulphonates having an alkyl chain length of $C_8$–$C_{15}$; primary and secondary alkylsulphates, particularly $C_8$–$C_{15}$ primary alkyl sulphates; alkyl ether sulphates; olefin sulphonates; alkyl xylene sulphonates; dialkyl sulphosuccinates; and fatty acid ester sulphonates. Sodium salts are generally preferred.

Nonionic surfactants that may be used include the primary and secondary alcohol ethoxylates, especially the $C_8$–$C_{20}$ aliphatic alcohols ethoxylated with an average of from 1 to 20 moles of ethylene oxide per mole of alcohol, and more especially the $C_{10}$–$C_{15}$ primary and secondary aliphatic alcohols ethoxylated with an average of from 1 to 10 moles of ethylene oxide per mole of alcohol. Non-ethoxylated nonionic surfactants include alkylpolyglycosides, glycerol monoethers, and polyhydroxyamides (glucamide).

Cationic surfactants that may be used include quaternary ammonium salts of the general formula $R_1R_2R_3R_4N^+X^-$ wherein the R groups are independently hydrocarbyl chains of $C_1$–$C_{22}$ length, typically alkyl, hydroxyalkyl or ethoxylated alkyl groups, and X is a solubilising cation (for example, compounds in which $R_1$ is a $C_8$–$C_{22}$ alkyl group, preferably a $C_8$–$C_{10}$ or $C_{12}$–$C_{14}$ alkyl group, $R_2$ is a methyl group, and $R_3$ and $R_4$, which may be the same or different, are methyl or hydroxyethyl groups); and cationic esters (for example, choline esters) and pyridinium salts.

The total quantity of detergent surfactant in the composition is suitably from 0.1 to 60 wt % e.g. 0.5–55 wt %, such as 5–50wt %.

Preferably, the quantity of anionic surfactant (when present) is in the range of from 1 to 50% by weight of the total composition. More preferably, the quantity of anionic surfactant is in the range of from 3 to 35% by weight, e.g. 5 to 30% by weight.

Preferably, the quantity of nonionic surfactant when present is in the range of from 2 to 25% by weight, more preferably from 5 to 20% by weight.

Amphoteric surfactants may also be used, for example amine oxides or betaines.

Builders:

The compositions may suitably contain from 10 to 70%, preferably from 15 to 70% by weight, of detergency builder. Preferably, the quantity of builder is in the range of from 15 to 50% by weight.

The detergent composition may contain as builder a crystalline aluminosilicate, preferably an alkali metal aluminosilicate, more preferably a sodium aluminosilicate.

The aluminosilicate may generally be incorporated in amounts of from 10 to 70% by weight (anhydrous basis), preferably from 25 to 50%. Aluminosilicates are materials having the general formula:

$$0.8\text{–}1.5\,M_2O.Al_2O_3.0.8\text{–}6\,SiO_2$$

where M is a monovalent cation, preferably sodium. These materials contain some bound water and are required to have a calcium ion exchange capacity of at least 50 mg CaO/g. The preferred sodium aluminosilicates contain 1.5–3.5 $SiO_2$ units in the formula above. They can be prepared readily by reaction between sodium silicate and sodium aluminate, as amply described in the literature.

Textile Softening and/or Conditioner Compounds As Carriers:

If the composition of the present invention is in the form of a textile conditioner composition, the textile-compatible carrier will be a textile softening and/or conditioning compound (hereinafter referred to as "textile softening compound"), which may be a cationic or nonionic compound.

The softening and/or conditioning compounds may be water insoluble quaternary ammonium compounds. The compounds may be present in amounts of up to 8% by weight (based on the total amount of the composition) in which case the compositions are considered dilute, or at levels from 8% to about 50% by weight, in which case the compositions are considered concentrates.

Compositions suitable for delivery during the rinse cycle may also be delivered to the textile in the tumble dryer if used in a suitable form. Thus, another product form is a composition (for example, a paste) suitable for coating onto, and delivery from, a substrate e.g. a flexible sheet or sponge or a suitable dispenser during a tumble dryer cycle.

Suitable cationic textile softening compounds are substantially water-insoluble quaternary ammonium materials comprising a single alkyl or alkenyl long chain having an average chain length greater than or equal to $C_{20}$. More preferably, softening compounds comprise a polar head group and two alkyl or alkenyl chains having an average chain length greater than or equal to $C_{14}$. Preferably the textile softening compounds have two, long-chain, alkyl or alkenyl chains each having an average chain length greater than or equal to $C_{16}$.

Most preferably at least 50% of the long chain alkyl or alkenyl groups have a chain length of $C_{18}$ or above. It is preferred if the long chain alkyl or alkenyl groups of the textile softening compound are predominantly linear.

Quaternary ammonium compounds having two long-chain aliphatic groups, for example, distearyldimethyl ammonium chloride and di(hardened tallow alkyl) dimethyl ammonium chloride, are widely used in commercially available rinse conditioner compositions. Other examples of these cationic compounds are to be found in "Surface-Active Agents and Detergents", Volumes I and II, by Schwartz, Perry and Berch. Any of the conventional types of such compounds may be used in the compositions of the present invention.

The textile softening compounds are preferably compounds that provide excellent softening, and are characterised by a chain melting Lβ to Lα transition temperature greater than 25° C., preferably greater than 35° C., most preferably greater than 45° C. This Lβ to Lα transition can be measured by DSC as defined in "Handbook of Lipid Bilayers", D Marsh, CRC Press, Boca Raton, Fla., 1990 (pages 137 and 337).

Substantially water-insoluble textile softening compounds are defined as textile softening compounds having a solubility of less than $1 \times 10^{-3}$ wt % in demineralised water at 20° C. Preferably the textile softening compounds have a solubility of less than $1 \times 10^{-4}$ wt %, more preferably less than $1 \times 10^{-8}$ to $1 \times 10^{-6}$ wt %.

Especially preferred are cationic textile softening compounds that are water-insoluble quaternary ammonium materials having two $C_{12-22}$ alkyl or alkenyl groups connected to the molecule via at least one ester link, preferably two ester links. An especially preferred ester-linked quaternary ammonium material can be represented by the formula III:

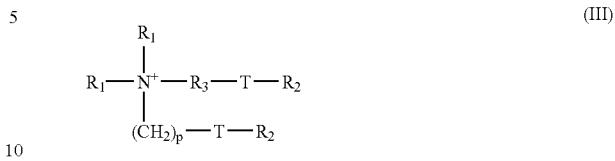

wherein each $R_1$ group is independently selected from $C_{1-4}$ alkyl or hydroxyalkyl groups or $C_{2-4}$ alkenyl groups; each $R_2$ group is independently selected from $C_{8-28}$ alkyl or alkenyl groups; and wherein $R_3$ is a linear or branched alkylene group of 1 to 5 carbon atoms, T is

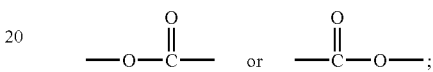

and p is 0 or is an integer from 1 to 5.

Di(tallowoxyloxyethyl) dimethyl ammonium chloride and/or its hardened tallow analogue is especially preferred of the compounds of formula (II).

A second preferred type of quaternary ammonium material can be represented by the formula (IV):

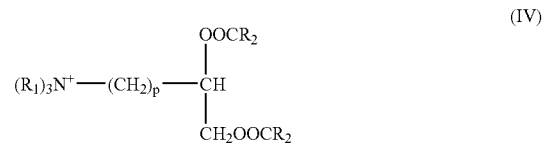

wherein $R_1$, p and $R_2$ are as defined above.

It is advantageous if the quaternary ammonium material is biologically biodegradable.

Preferred materials of this class such as 1,2-bis(hardened tallowoyloxy)-3-trimethylammonium propane chloride and their methods of preparation are, for example, described in U.S. Pat. No. 4,137,180 (Lever Brothers Co). Preferably these materials comprise small amounts of the corresponding monoester as described in U.S. Pat. No. 4,137,180, for example, 1-hardened tallowoyloxy-2-hydroxy-3-trimethylammonium propane chloride.

Other useful cationic softening agents are alkyl pyridinium salts and substituted imidazoline species. Also useful are primary, secondary and tertiary amines and the condensation products of fatty acids with alkylpolyamines.

The compositions may alternatively or additionally contain water-soluble cationic textile softeners, as described in GB 2 039 556B (Unilever).

The compositions may comprise a cationic textile softening compound and an oil, for example as disclosed in EP-A-0829531.

The compositions may alternatively or additionally contain nonionic textile softening agents such as lanolin and derivatives thereof.

Lecithins are also suitable softening compounds.

Nonionic softeners include Lβ phase forming sugar esters (as described in M Hato et al Langmuir 12, 1659, 1666, (1996)) and related materials such as glycerol monostearate or sorbitan esters. Often these materials are used in conjunction with cationic materials to assist deposition (see, for example, GB 2 202 244). Silicones are used in a similar way as a co-softener with a cationic softener in rinse treatments (see, for example, GB 1 549 180).

The compositions may also suitably contain a nonionic stabilising agent. Suitable nonionic stabilising agents are linear $C_8$ to $C_{22}$ alcohols alkoxylated with 10 to 20 moles of alkylene oxide, $C_{10}$ to $C_{20}$ alcohols, or mixtures thereof.

Advantageously the nonionic stabilising agent is a linear $C_8$ to $C_{22}$ alcohol alkoxylated with 10 to 20 moles of alkylene oxide. Preferably, the level of nonionic stabiliser is within the range from 0.1 to 10% by weight, more preferably from 0.5 to 5% by weight, most preferably from 1 to 4% by weight. The mole ratio of the quaternary ammonium compound and/or other cationic softening agent to the nonionic stabilising agent is suitably within the range from 40:1 to about 1:1, preferably within the range from 18:1 to about 3:1.

The composition can also contain fatty acids, for example $C_8$ to $C_{24}$ alkyl or alkenyl monocarboxylic acids or polymers thereof. Preferably saturated fatty acids are used, in particular, hardened tallow $C_{16}$ to $C_{18}$ fatty acids. Preferably the fatty acid is non-saponified, more preferably the fatty acid is free, for example oleic acid, lauric acid or tallow fatty acid. The level of fatty acid material is preferably more than 0.1% by weight, more preferably more than 0.2% by weight. Concentrated compositions may comprise from 0.5 to 20% by weight of fatty acid, more preferably 1% to 10% by weight. The weight ratio of quaternary ammonium material or other cationic softening agent to fatty acid material is preferably from 10:1 to 1:10.

Textile Treatment Product Forms

The composition of the invention may be in the form of a liquid, solid (e.g. powder or tablet), a gel or paste, spray, stick or a foam or mousse. Examples include a soaking product, a rinse treatment (e.g. conditioner or finisher) or a main-wash product. The composition may also be applied to a substrate e.g. a flexible sheet or used in a dispenser which can be used in the wash cycle, rinse cycle or during the dryer cycle.

Liquid compositions may also include an agent which produces a pearlescent appearance, e.g. an organic pearlising compound such as ethylene glycol distearate, or inorganic pearlising pigments such as microfine mica or titanium dioxide ($TiO_2$) coated mica.

Liquid compositions may be in the form of emulsions or emulsion precursors thereof.

The composition of the invention may further comprise a silicone component. It is preferred if the silicone component is a dimethylpolysiloxane with amino alkyl groups. It may be used in the context of the present invention as an emulsion in water.

It is preferred if the silicone component is present in a ratio of first component: silicone of from 1:1 to 30:1, preferably 1:1 to 20:1, more preferably 2:1 to 20:1 and most preferably 5:1 to 15:1.

Silicone suitable for use in textile conditioning compositions include predominately linear polydialkylsiloxanes, e.g. polydimethylsiloxanes or aminosilicones containing amine-functionalised side chains.

Composition may comprise soil release polymers such as block copolymers of polyethylene oxide and terephthalate.

Other optional ingredients include emulsifiers, electrolytes (for example, sodium chloride or calcium chloride) preferably in the range from 0.01 to.5% by weight, pH buffering agents, and perfumes (preferably from 0.1 to 5% by weight).

Further optional ingredients include non-aqueous solvents, perfume carriers, fluorescers, colourants, hydrotropes, antifoaming agents, antiredeposition agents, enzymes, optical brightening agents, opacifiers, dye transfer inhibitors.

In addition, compositions may comprise one or more anti-spotting agents, germicides, fungicides, anti-oxidants, UV absorbers (sunscreens), heavy metal sequestrants, chlorine scavengers, dye fixatives, anti-corrosion agents, drape imparting agents, antistatic agents and ironing aids. The lists of optional components are not intended to be exhaustive.

The invention will now be described by way of example only and with reference to the following non-limiting examples.

EXAMPLES

Example 1

Method of Preparation of Voranol Iso-thiouronium Compounds

Voranol CP3055 ™ (ex-Dow Chemicals) (29.4 g, 0.01 moles, mw 2940) was dissolved in toluene 50 mls. To this was added 3-bromopropionic acid (4.95 g, 3.3 equivalents Aldrich) and p-toluene sulphonic acid (1 g) to act as an acid catalyst. The solution was stirred by means of a magnetic follower on a hot plate. The solution was refluxed with a Dean and Stark distillation trap. After 1.5 hours no more water was seen to azeotrope from the reaction vessel into the side arm. The reaction was stopped and allowed to cool.

The toluene/Voranol solution was shaken with solution of sodium bicarbonate (10 g/l). This was repeated five times, until the solution was seen not to fizz from the evolution of carbon dioxide gas and the water was at a neutral pH. The two phases were separated and the toluene was removed from the Voranol compound by rotary evaporation. After drying in vacuo over calcium chloride the yield was 29.28 g (theoretical yield is 33.44 g). The losses were mainly due to the highly viscous sticky nature of the polymer which stuck to glass ware. A pale yellow liquid product was obtained. FT-IR analysis confirmed the presence of an ester group by showing a new peak at 1737 $cm^{-1}$ The product from the previous step was dissolved in ethanol (50 mls). To this solution was added thiourea (2.28 g 0.03 m Aldrich). This solution was then refluxed for six hours and cooled. The product was not isolated since the thick viscous nature of the pure product made it very difficult to handle.

Addition of the compound to an aqueous solution at a pH below 4 gave a water-soluble product. At pH above pH8, the product is converted from the isothiouronium to produce a thiol group. This step results in the precipitation of the polymer and an opaque, cloudy solution was observed.

Addition of the compound to a solution containing an anionic compound e.g. sodium dodecyl sulphate under acidic conditions leads to the precipitation of a white sticky mass.

The formation of a thiol was determined by the use of Ellmans reagent, which reacts with thiol compounds forming an orange coloured solution. The formation and use of Ellmans reagent is described in Practical Protein Chemistry, A Darbre, Wiley Interscience, New York 1970.

Isolation of a small quantity of isothiouronium polymer for FT-IR analysis confirmed the structure by the presence of new peaks correlating to the structure of isothiouronium groups.

Example 2

Experimental Procedure to Show Effect on Fibre Damage

Experiments were performed with pigment-printed, woven, cotton, red and black, striped cloth. This was laundered in an unmodified AEG Lavamat 50700 ™ washing machine on a cotton cycle at 40 Celsius. The isothiouronium compound prepared according to the method described in example 1 was introduced during the rinse cycle. After laundering, the samples were dried at 50 Celsius in a fan oven for 20 minutes.

Samples which had been laundered up to five times were shown to a panel of independent observers for assessment of damage. Samples were observed in a light cabinet under D65 illumination. All of the observers were of the opinion that samples treated according to the method of the invention were less damaged than controls. Damage was also measured using the gray scale measurement as detailed in BS1006/A02:1990. Results were as given below in Table 1.

From Table 1 it can be seen that there is a significant reduction in the level of damage as assessed by this method for embodiments of the invention.

The least damage occurred when the protected thiol (isothiouronium) polymers were used together with azetidinium-containing polymers.

TABLE 1

Grey scale ratings for repeated washings of cloth with control and according to an embodiment of the method of the invention.

| Treatment | Wash 1 | Wash 2 | Wash 3 | Wash 4 | Wash 5 |
|---|---|---|---|---|---|
| Untreated | 3 | 2–3 | 2–3 | 2 | 2 |
| 0.5% Voranol isothiouronium (Ex. 1) | 3–4 | 3–4 | 3–4 | 3 | 3 |
| 1.0% Voranol isothiouronium (Ex. 1) | 3–4 | 3–4 | 3–4 | 3–4 | 3 |
| 0.5% Voranol isothiouronium (Ex. 1) + 0.5% Listrilan azetidinium | 4–5 | 4–5 | 4 | 4 | 4 |
| 1.0% Voranol isothiouronium (Ex. 1) + 1.0% Listrilan azetidinium | 4–5 | 4–5 | 4–5 | 4–5 | 4 |

What is claimed is:

1. A process for the laundering of non-keratinaceous textiles, which comprises the step of laundering the textiles with a composition comprising:
   a) a self-crosslinking cationic polymer;
   b) a nucleophilic species capable of reacting with polymer;
   c) a textile compatible carrier;
   d) wherein the nucleophilic species comprises a protecting group which is sufficiently labile that it leaves when the polymer and the laundered textiles are exposed to a pH of above 8 at a temperature of below 50 Celsius; and
   e) wherein the composition comprises a detergent active compound in the concentration of 5 to 50 wt. %.

2. A process according to claim 1, wherein the textile comprises cotton or regenerated cellulose.

3. A process according to claim 1, wherein the composition further comprises a textile softening and/or conditioning compound.

4. A process according to claim 1 wherein the nucleophile is a polymer comprising at least one protected thiol group, wherein the protecting group is labile under domestic washing conditions.

5. A process according to claim 4, wherein the protected thiol comprises a terminal or mid chain isothiouronium group.

6. A process according to claim 1 wherein the nucleophile is present in the composition in an amount such that from 0.0005% to 5% by weight on weight of textile is provided.

7. A process according to claim 1 wherein the self-crosslinking cationic polymer comprises a polymer having azetidinium groups and/or one or more functional groups capable of forming azetidinium groups.

8. A process according to claim 7 wherein the composition comprises an amine or amide-epichlorohydrin resin having one or more azetidinium functional groups.

9. A process as claimed in claim 1, wherein the composition is applied to the textile during the rinse cycle of the laundering process.

10. A detergent composition for use in the process of claim 1 characterized in that the composition comprises:
   a) a self-crosslinking cationic polymer;
   b) a nucleophilic species capable of reacting with polymer (a);
   c) a textile compatible carrier;
   d) wherein the nucleophilic species comprises a protecting group which is sufficiently labile that it leaves when the polymer and the laundered textiles are exposed to a pH of above 8 at a temperature of below 50 Celsius; and
   e) wherein the composition comprises a detergent active compound in the concentration range of 5 to 50 wt. %.

* * * * *

UNITED STATES PATENT AND TRADEMARK OFFICE
CERTIFICATE OF CORRECTION

| | |
|---|---|
| PATENT NO. | : 7,091,172 B2 |
| APPLICATION NO. | : 10/450076 |
| DATED | : August 15, 2006 |
| INVENTOR(S) | : Oakes et al. |

It is certified that error appears in the above-identified patent and that said Letters Patent is hereby corrected as shown below:

Column 16, lines 6 and 7, please change "b) a nucleophilic species capable of reacting with polymer;" to:

-- b) a nucleophilic species capable of reacting with polymer (a); --

Signed and Sealed this

Twenty-seventh Day of March, 2007

JON W. DUDAS
*Director of the United States Patent and Trademark Office*